United States Patent
Zhang et al.

(10) Patent No.: US 8,721,842 B2
(45) Date of Patent: May 13, 2014

(54) CATALYTIC REACTION-RECTIFICATION INTEGRATED PROCESS AND SPECIALIZED DEVICE THEREOF

(75) Inventors: Zhibing Zhang, Nanjing (CN); Zheng Zhou, Nanjing (CN); Youting Wu, Nanjing (CN); Min Shao, Nanjing (CN)

(73) Assignee: Nanjing University (CN)

( * ) Notice: Subject to any disclaimer, the term of this patent is extended or adjusted under 35 U.S.C. 154(b) by 751 days.

(21) Appl. No.: 12/745,709

(22) PCT Filed: Nov. 20, 2008

(86) PCT No.: PCT/CN2008/001895
§ 371 (c)(1),
(2), (4) Date: Jun. 2, 2010

(87) PCT Pub. No.: WO2009/079909
PCT Pub. Date: Jul. 2, 2009

(65) Prior Publication Data
US 2011/0144378 A1 Jun. 16, 2011

(30) Foreign Application Priority Data
Dec. 5, 2007 (CN) .......................... 2007 1 0191016

(51) Int. Cl.
| | | |
|---|---|---|
| *B01D 3/14* | (2006.01) | |
| *B01J 8/00* | (2006.01) | |
| *B01J 10/00* | (2006.01) | |
| *C07C 67/08* | (2006.01) | |
| *C07C 67/48* | (2006.01) | |
| *C07C 29/80* | (2006.01) | |
| *C07C 41/42* | (2006.01) | |

(52) U.S. Cl.
USPC ............ 203/29; 159/25.2; 202/158; 202/175; 202/186; 202/265; 203/14; 203/41; 203/87; 203/DIG. 6; 422/187; 422/223; 422/291; 422/305; 422/610; 366/342; 560/248; 568/697

(58) Field of Classification Search
USPC ............ 203/14, 29, 41, 87, DIG. 6; 202/158, 202/175, 186, 200, 265; 422/187, 211, 223, 422/291, 305, 610; 159/25.2; 366/342; 568/697; 560/248
See application file for complete search history.

(56) References Cited

U.S. PATENT DOCUMENTS

| | | | | |
|---|---|---|---|---|
| 5,776,320 | A  * | 7/1998 | Marion et al. ................... | 203/29 |
| 6,149,879 | A  * | 11/2000 | Forestiere et al. ............ | 422/607 |
| 6,392,078 | B1 * | 5/2002 | Ryu et al. ...................... | 558/277 |
| 7,531,142 | B2 * | 5/2009 | Huziwara et al. ............. | 422/143 |
| 2002/0133050 | A1 | 9/2002 | Chuang et al. | |
| 2004/0124124 | A1* | 7/2004 | Pinho et al. ................... | 208/113 |

FOREIGN PATENT DOCUMENTS

| | | |
|---|---|---|
| CN | 1064475 | 9/1992 |
| CN | 1511819 | 7/2004 |
| CN | 101254444 | 9/2008 |

* cited by examiner

*Primary Examiner* — Virginia Manoharan
(74) *Attorney, Agent, or Firm* — Schmeiser, Olsen & Watts, LLP

(57) ABSTRACT

A catalytic reaction-rectification integrated process and a catalytic reaction-rectification integrated column, and the specialized device of such process is provided. The reactants are preheated and mixed with catalysts, and then fed into a jet agitation reaction section located in the middle of the catalytic reaction-rectification integrated column from a feeding inlet. The jet agitation reaction section is a kettle-like reactor located in the middle of the catalytic reaction-rectification integrated column. After pressurized by a centrifugal pump, the reactant materials are admitted into a subsonic or transonic agitator located within the reaction section. The reactant materials are ejected into the jet agitation reaction section at high speed, to efficiently mix the solid and liquid phases in the reaction section and to reinforce heat and mass transfer efficiency during the reaction. The liquid reaction mixture is separated and purified directly in the catalytic reaction-rectification integrated column.

7 Claims, 3 Drawing Sheets

CATALYTIC REACTION-RECTIFICATION INTEGRATED PROCESS AND SPECIALIZED DEVICE THEREOF

CROSS-REFERENCE TO RELATED APPLICATIONS

This application claims priority to PCT Application No. PCT/CN08/001895, having an international filing date of Nov. 20, 2008, pursuant to U.S.C. §365.

FIELD OF TECHNOLOGY

This invention relates to a new catalytic reaction-rectification integrated process, specifically, it integrates catalytic reaction process and rectification process.

BACKGROUND

Esters and ethers, such as ethyl formate, ethyl acetate, butyl acetate, methyl lactate and MTBE (methyl tertiary butyl ether), etc., are among important raw materials in the chemical industry. Esters, for example, ethyl acetate and butyl acetate, are used in paints, fragrances, and as intermediates for organic synthesis as well as solutions for many organic compounds; they can also be used either as extractants or as fragrant components in petroleum processing and pharmaceutical industries. Methyl lactate is another important fine chemical for organic chemical industry, widely used as raw material in food, beverage and medicine fields. It is a green solution being non-toxic, non-volatile, highly soluble, and highly degenerable, which ensures it an optimistic market prospect. The hydrolysis of methyl lactate is also the most favorable way to obtain high-purity polylactic acid. MTBE, when used as an additive to lead-free gas, shows high anti-explosion performance, high compatibility, less water absorption and no pollution to environment. During the most recent 10 years, along with restriction on application of lead tetraethide, MTBE has become increasingly widely used. Besides, in order to increase production efficiency, cut down on energy consumption and improve safety of production environment, the technique in the catalytic reaction and its corresponding separation process—widely applied in the oxidation/peroxidation and separation process of olefins and alkanes in petrochemical industry, hydration and separation of olefins, and many other hydrogenating reactions—should be further improved and reinforced.

Taking production of NBAC (n-butyl acetate) as an example, the traditional technique is taking sulfuric acid or sulfonic acid ion exchange resin as catalyst and producing NBAC through the rhythmic reaction or fixed-bed reaction. There are many defects in these methods. As to the rhythmic reaction, the defects are low efficiency, erosive damage of equipments caused by sulfuric acid, and unreusability of catalyst due to necessary neutralization of acid during the separation process. When solid acid catalyst and fixed-bed reaction is adopted, the whole process is not only time-consuming, but also low in conversion rate (about 50%). The process also requires a large quantity of butanol as the raw material, which consequently complicates the separation process thereafter and increases production cost as well. Due to these reasons, both the primary investment of the whole set of equipments and later maintenance cost keep considerably high, which calls for new production processes.

SUMMARY

The present invention presents a reinforced catalytic reaction-rectification integrated system that integrates a subsonic or transonic jet agitation reaction section and a rectification column. This system is particularly suitable to produce esters through esterification, alcohols through hydration, dehydration of alcohols, or ethers through additive reaction of enols. It is also applicable in hydrogenation and separation processes in petrochemical industry as well as various oxidation/peroxidation and separation processes of olefins and alkanes. The catalyst used in this system can be either solid or liquid, and according to different separation requirements of reactant mixture, the single- or multiple-column process can be adopted. The whole system can effectively decrease energy consumption, dramatically increase reaction and separation efficiency, remarkably save construction investment and improve safety of production environment.

The present invention reaches the aforesaid goal through following technical details:

A process integrating catalytic reaction and rectification, as is shown in FIG. 1, comprising following steps:

Step 1. two reactants separately stored in storage tanks (G-01 and G-02) are led to preheaters (1 and 2) and preheated therein respectively. After being mixed with the catalyst, the reactants are fed into the jet agitation reaction section (6) of the catalytic reaction-rectification integrated column (T-01). The jet agitation reaction section looks like a reaction kettle, located in the middle of the catalytic reaction-rectification integrated column (T-01);

Step 2. the reactants in the jet agitation reaction section (6) then flow through filtering bottom socket and the pipe (6-21) to the centrifugal pump (21); after being pressurized by the pump (21), they go through the heat exchanger (15) for heating or cooling; thereafter they are led into the subsonic or transonic jet agitator (33) of the jet-agitation reaction section (6); the reactants are jetted into the reaction section (6) at high speed, and the solid and the liquid in the reaction section are efficiently mixed; this method can also increase efficiency in heat and mass transfer so that the reaction speed, conversion rate and even selectivity can be highly increased. The working mechanism is that, when the method is adopted, the fluid's circulation rate in the reaction section is much higher (10-20 times) than its real volume can stir, which consequently results in a highly forced vortex within the reaction section. The solid (or powder) catalyst, driven by the vortex, suspends in the liquid reactants and moves randomly therein. This makes the whole reaction section act like a perfect mixing reaction kettle. Therefore, the contact between reactants, molecules and catalyst grains as well as that between molecules of different reactants are perfectly guaranteed, through which the ideal state of heat and mass transfer will be obtained. Since intermolecular diffusion rate is highly increased, the whole reaction rate and conversion rate can be effectively increased. In addition, it can also inhibit most of side reactions that may occur in the abovementioned reactions, which in turn increases selectivity of reaction as a whole;

Step 3. there exists a filtering overflow pipe (7) in the reaction section (6); when the fluid therein reaches a certain level, it overflows down through the pipe (6-9) into the liquid distributor (8) at the lower part of the catalytic reaction-rectification integrated column (T-01); after being well distributed therein, the fluid goes into the stripping section (9) of the catalytic reaction-rectification integrated column (T-01);

Step 4. the fluid is fractionally distilled and separated in the stripping section (9) of the catalytic reaction-rectification integrated column (T-01), and thereafter is channeled out from the bottom of the column; part of the fluid is led to the stripping column (T-03) for further separation while the rest is heated into steam by the reboiler (10), and is subsequently channeled back to the stripping section (9) of the catalytic reaction-rectification integrated column (T-01);

Step 5. the gas emitting up from the stripping section (9) of the catalytic reaction-rectification integrated column (T-01) is led through the pipe (9-4) and the air distributor (5) back to the rectification section (4) of the catalytic reaction-rectification integrated column (T-01) for further separation, while the precipitating fluid in the rectification section (4) directly flows into the reaction section (6) of the catalytic reaction-rectification integrated column (T-01) for further processing; the gas separated by the rectification section (4) is condensed into liquid by the condenser (12) at the column top; the condensed liquid then goes into oil-water separator (11) for oil-water phase-splitting; the oil-phase components flow back to the top of the rectification section of the catalytic reaction-rectification integrated column (T-01) while the water-phase components are channeled through the pipe (11-T-02) into dehydration column (T-02), wherein the water-phase components are dehydrated so that the oil-phase components can be further extracted from the fluid; the fluid that is channeled into the dehydration column (T-02) is mainly water, containing a little amount of oil-phase organics;

Step 6. After being separated through dehydration in the dehydration column (T-02), the fluid (oily water) is led to the column top, wherein it is condensed by the condenser (22) and channeled to oil-water separator (23) for phase-splitting; thereafter the water-phase components flow back to the top of the dehydration column (T-02) while the oil-phase components flow back to the rectification section (4) of the catalytic reaction-rectification integrated column (T-01) through the pipe (23-4); the water (99.5% water, 0.5% organics) that flows back to the dehydration column (T-02), after being upgradingly purified, is discharged through the pipe (28) at the bottom of the dehydration column (T-02);

Step 7. after step 4 abovementioned, the fluid is further separated by the rectification column (T-03); the gas obtained thereof is condensed into liquid by the condenser (25) at the column top; the liquid then comes into the collector (26), part of which flows back while the rest returns to the reaction section (6) of the column (T-01) again; the fluid at the bottom of the rectification column (T-03) is high boiling point distillate, part of which is channeled back to the storage tank through the pipe (29) at the bottom of the column, while the rest is heated into steam by the reboiler (27) and led to the bottom of the rectification column (T-03).

This catalyst used in the abovementioned catalytic reaction-rectification system needs to be changed after a certain period of operation, and the steps includes:

Step 1. turn on both the valve (16) on the pipe connecting the bottom of the reaction section (6) and the catalyst solid-liquid separation tank (20) and the valve (17) on the pipe connecting the catalyst solid-liquid separation tank (20) and the centrifugal pump (21); turn off the valve (14) on the pipe connecting the bottom of the reaction section and the centrifugal pump (21); in the catalyst solid-liquid separation tank (20) secures the high-performance filtering mesh (19), which retains the solid catalyst grains in the fluid while lets go the fluid; the fluid then is pumped back to the reaction section through the pipe (21-6) by the pump (21);

Step 2. turn off both the valve (16) and the value (17) after the catalyst in the reaction section (6) is completely channeled into the catalyst solid-liquid separation tank (20);

Step 3. there are a catalyst feeding equipment (3) on the pipe connecting the storage tanks (G-01 and G-02) and the reaction section (6) of the catalytic reaction-rectification integrated column (T-01); open the cover of the catalyst feeding equipment (3) and add new catalyst grains; then close the cover;

Step 4. turn on the valve of the catalyst feeding equipment (3); turn on the valve (30) on the pipe connecting the storage tanks (G-01 and G-02) and the reaction section (6) of the catalytic reaction-rectification integrated column (T-01); along with the current of liquid reactants from the tanks to the reaction section, the catalyst grains in the catalyst feeding equipment (3) is flushed into the reaction section (6) of the catalytic reaction-rectification integrated column (T-01);

Step 5. turn off the valve of the catalyst feeding equipment (3) and the valve (30); remove the old catalyst from the catalyst solid-liquid separation tank (20); the whole procedure of changing catalyst is accomplished. The catalytic reaction-rectification system resumes its normal process.

The catalyst change procedure of this system can be easily conducted at one stroke. There is no gas or liquid leak during the operation, and the working process of the whole system is not interfered.

The process integrating catalytic reaction and rectification as defined above can be adopted to produce esters through combination of acids and alcohols, alcohols through hydration of olefins, or ethers through combination of olefins and alcohols.

A catalytic reaction-rectification integrated column specially designed for the catalytic reaction-rectification integrated process as defined above, comprising three sections: the upper rectification section (4), the middle jet agitation reaction section (6) and the lower stripping section (9); the rectification section is actually a fractional distilling column in the form of either a plate column or a packing column; considering the Maragoni Effect, the plate column is a better choice; at the bottom of the rectification section (4) exists an air distributor (5) while at the top of which exist a condenser (12) and oil-water separator; the jet agitation reaction section (6) has a base and a top cover that can be either porous or airtight; at the upper part of the jet agitation reaction section exist a feeding inlet and a feeding pipe; in the middle of the jet agitation reaction section exist a subsonic or transonic jet agitator and a filtering pipette, which connects to the centrifugal pump (21); the outlet of the pump (21) connects to the jet agitator; when starting the centrifugal pump (21), the fluid in the jet agitation reaction section will circulate therein continuously, and strong jet reaction occurs as well; in the jet agitation reaction section (6) also exists a filtering overflow pipe (7) that connects to the liquid distributor (8) at the top of the stripping section (9); when the fluid in the reaction section (6) reaches a certain level, it automatically overflows down to the liquid distributor (8) at the top of the stripping section (9), then to the stripping section (9); the stripping section (9) is also a fractional distilling column in the form of either a plate column or a packing column; in order to keep lower pressure drop in the stripping section (9), the packing column is a better choice; on the base of the column (9) connects a pipe that channels out the primarily processed fluid, part of which is reheated by the reheater (10) and flows back to the lower part of the stripping section (9); it provides heat energy for the stripping section so that the fractional distilling process can run smoothly; the steam at the upper part of the stripping section (9), via the outer pipe (9-4), is led to the air distributor (8) at the bottom of the rectification section (4); the steam is rectified therein; the high boiling point distillate at the bottom of the rectification section (4) then flows back to the jet agitation reaction section (6);

A catalytic reaction-rectification integrated column as defined above, wherein on the feeding pipe that is on the top of the jet agitation reaction section (6) secures a catalyst feeding equipment (3) and a valve; at the bottom of the column exists a pipe connecting to the catalyst solid-liquid separator (20), which has a pipe connecting to the centrifugal pump (21); there is high-performance filtering mesh in the catalyst solid-liquid separator (20) for changing catalyst.

The characteristics that distinguishes this process from those currently existing ones are: (1) in the middle of the column exists a perfect mixing reaction kettle; it, together with a high-speed jet pump, pipe, a heat exchanger, a circulation pump and a filtering overflow pipe, forms a high-speed liquid jet agitation mixture system; (2) addition and withdrawal of heat can be easily and promptly conducted through the heating and cooling system composed of the circulation pump and the heat exchanger connecting to the outer pipe; so the temperature of reaction can be desirable adjusted; (3) the catalyst change is more convenient thanks to the catalyst change system that comprises the circulation pump and the catalyst solid-liquid separation tank (20); there is no gas or liquid leak during the change, and the working process of the whole system is not interfered; (4) the liquid-phase reactants in the jet agitation reaction kettle of the reaction-rectification integrated column overflow down to the stripping section of the column, while the gas-phase reactants emit up to the rectification section of the column; the gas created in the stripping section goes through the bypass pipe up into the rectification section while the liquid in the stripping section is directly channeled back to the jet agitation reaction kettle for further processing; (5) the system disclosed in the present invention is applicable to those non-esterification reactions abovementioned as long as the structure and number of the separation columns need some proper adjustments, this therefore shows the advantages of this system: (1) since the end-product is continuously removed out of the reaction kettle, the reaction balance point moves toward the product side, which consequently increases the conversion rate; (2) the heat energy engendered in the reaction section is directly reused by the rectification section, which cut down on energy consumption; (3) the two procedures, reaction and rectification, can be simultaneously accomplished within one column, which saves equipment investment; (4) the jet agitator used in this invention can repeatedly jet the gas over the reactants (normally solid-liquid mixture) down to the bottom of the kettle, which increases the utilization rate of raw materials, particularly useful for hydrogenation or oxidation that involves gas-phase reactants; (5) the catalyst grains suspend within the liquid-phase reactants and flow with them in the jet agitation reaction kettle, which ensures ideal contact between catalyst and reactants and expedites reaction process.

Taking production of butyl acetate as an example, compared with the traditional method—sulfuric acid catalysis, the process disclosed in this invention can double the production capacity and achieve 10% increase in the conversion rate, despite the same scale of equipments. The erosive damage of equipments can be dramatically relieved, and the overall production cost drops about 30% accordingly.

DETAILED DESCRIPTION OF THE DRAWINGS

Figure 1:
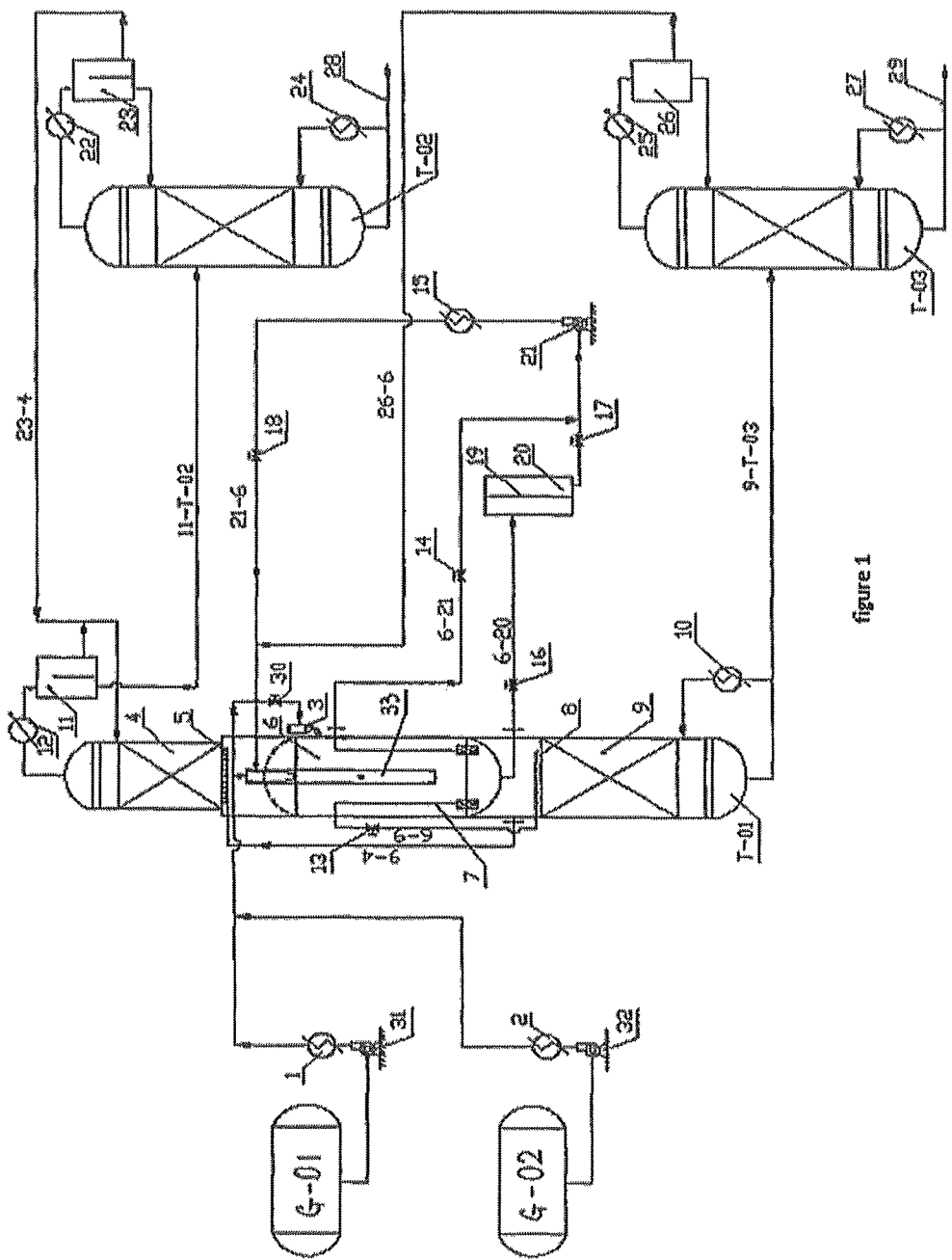
FIG. 1 depicts a general illustration of a first embodiment.

FIG. 1 is the general illustration of the present invention as well as that of Embodiment 1, therein:

1, 2 preheaters of feeding materials (acetic acid and n-butanol respectively); 3 catalyst feeding equipment; 4 rectification section of Column T-01; 5 air distributor, 6 reaction section; 7 filtering overflow pipe; 8 liquid distributor; 9 stripping section of Column T-01; 10, 24 and 27 reboilers; 11 and 23 oil-water separators; 12, 22 and 25 condensers at the column top; 13, 14, 16, 17, 18 and 30 valves; 9-4, 6-9, 6-20, 6-21, 9-T-02, 11-T-02, 26-6, 23-4 and 21-6 pipes; 15 heat exchanger; 19 filtering mesh; 20 filtering tank; 21, 31 and 32 pumps; 26 collectors for condensed liquid; 28 water outlet; 29 butyl acetate outlet; 33 jet agitator.

Figure 2:
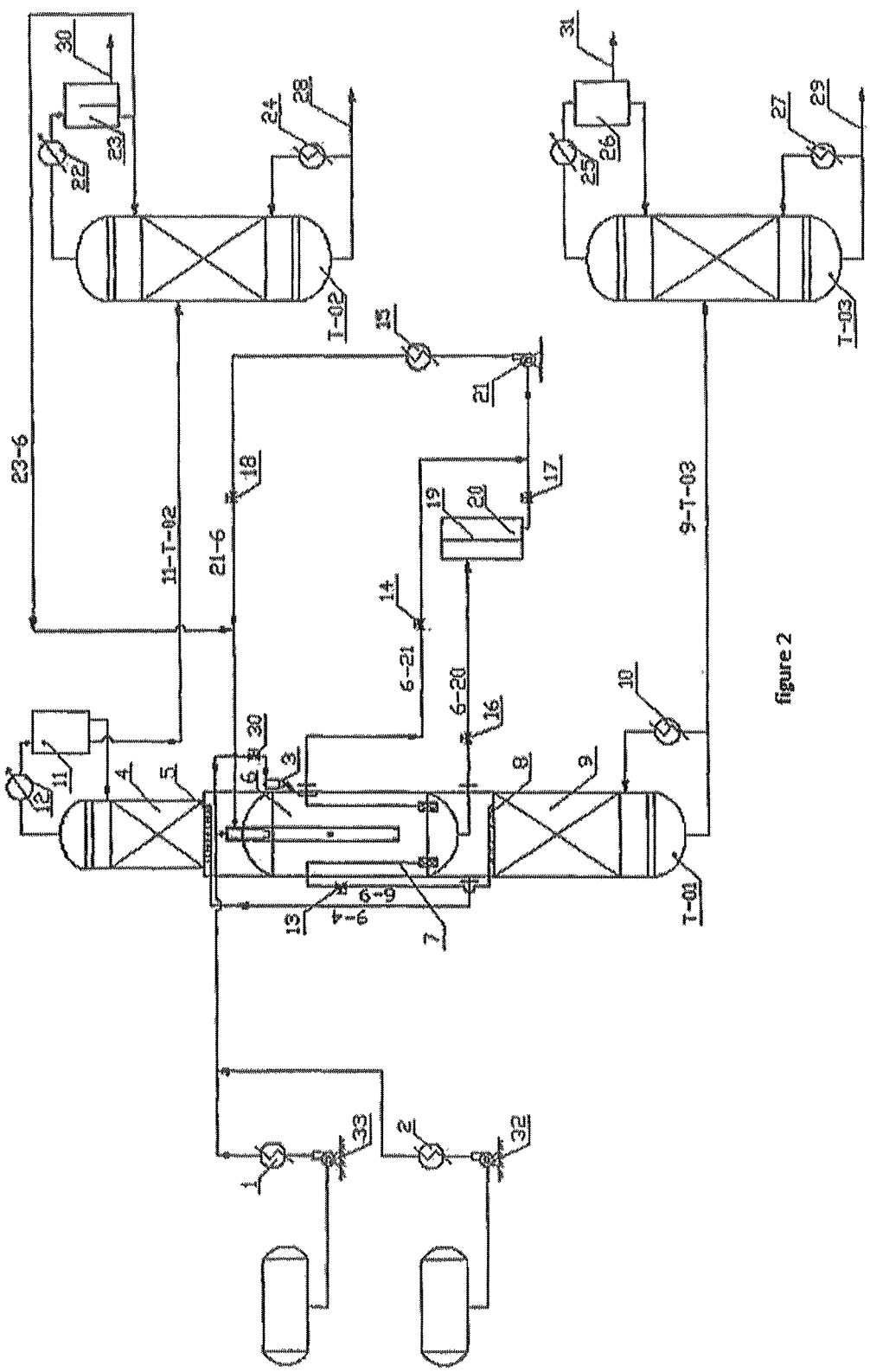
FIG. 2 depicts a general illustration of a second embodiment.

FIG. 2 is the illustration of Embodiment 2, therein
1, 2 preheaters of feeding materials (dihydromyrcene and water respectively); 3 catalyst feeding equipment; 4 rectification section of Column T-01; 5 air distributor, 6 reaction section; 7 filtering overflow pipe; 8 liquid distributor; 9 stripping section of Column T-01; 10, 24 and 27 reboilers; 11 and 26 condensed liquid collectors; 12, 22 and 25 condensers at the column top; 13, 14, 16, 17, 18 and 30 valves; 9-4, 6-9, 6-20, 6-21, 9-T-03, 11-T-02, 23-6 and 21-6 pipes; 15 heat exchanger; 19 filtering mesh; 20 filtering tank; 21, 32 and 33 pumps; 28 water outlet; 29 outlet for heavy organic components; 30 outlet for light organic components; 31 dihydromyrecenol outlet; 34 jet agitator.

Figure 3:
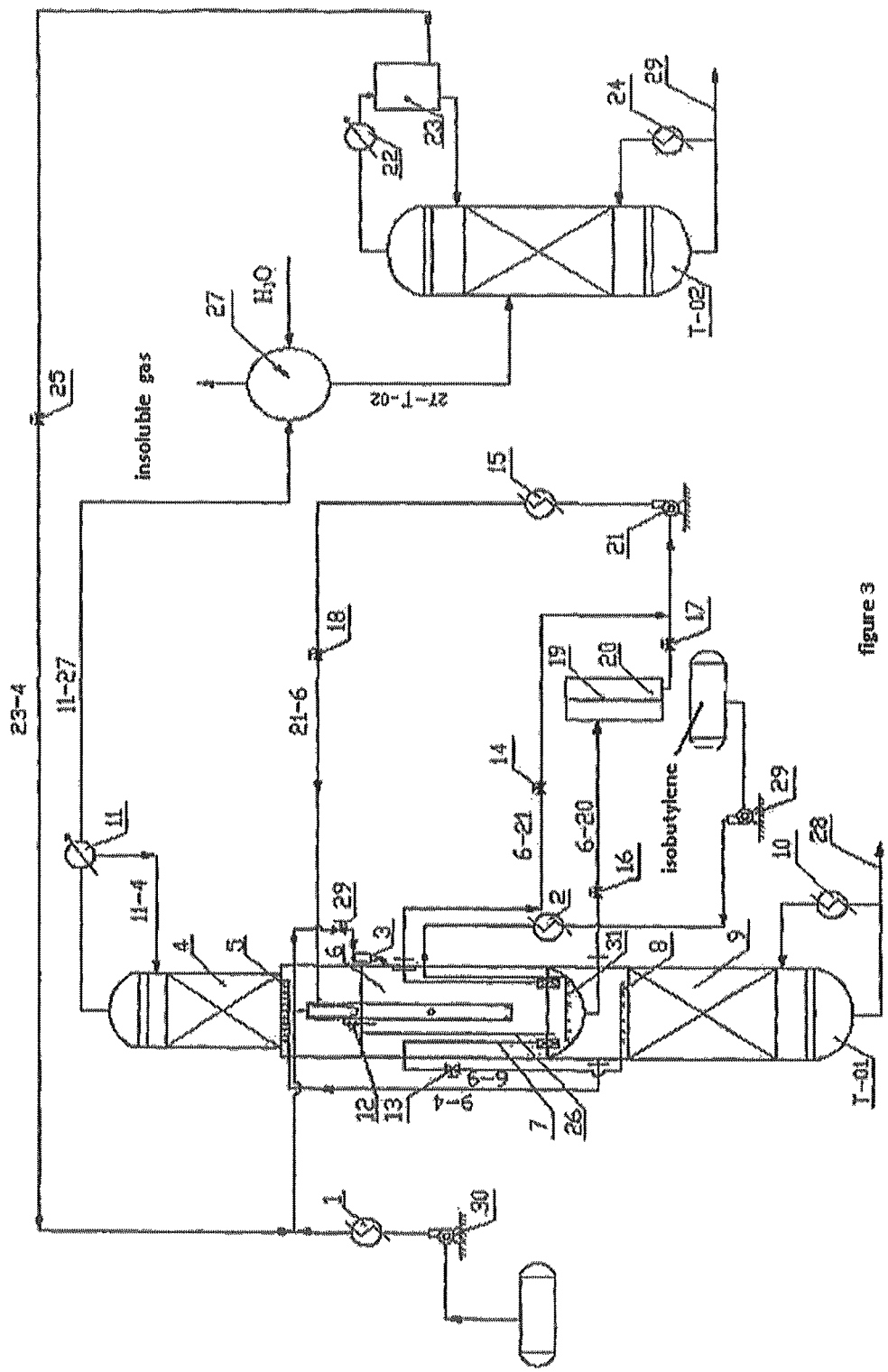
FIG. 3 depicts a general illustration of a third embodiment.

FIG. 3 is the illustration of Embodiment 3, therein:
1, 2 preheaters of feeding materials (methanol and isobutylene respectively); 3 catalyst feeding equipment; 4 rectification section of Column T-01; 5 and 31 air distributor, 6 reaction section; 7 filtering overflow pipe; 8 liquid distributor; 9 stripping section of Column T-01; 10 and 24 reboilers; 11 partial condenser; 12 gas-phase pipe 13, 14, 16, 17, 18, 25 and 29 valves; 21, 29 and 30 pumps; 9-4, 6-9, 6-20, 6-21, 11-4, 11-27, 27-T-02, 23-4 and 21-6 pipes; 15 heat exchanger; 19 filtering mesh; 20 filtering tank; 22 condenser at the column top; 23 condensed liquid collector; 26 liquid-phase pipe; 27 washer; 28 TMBE outlet; 29 water outlet; 33 jet agitator.

EMBODIMENTS

The followings are embodiments of the present invention.

Embodiment 1

Production of Butyl Acetate through Esterification (3-Column System)

FIG. 1 illustrates the configuration of the whole manufacturing system, wherein the catalytic reaction-rectification integrated column (T-01) is 0.4 m in diameter and 12 m in height, wherein the reaction section (6) is 1.5 m in height while the rectification section (4) 4.5 m and the stripping section (9) (including the column kettle) 6 m; heat-resistant, high-acidic ion exchange resin is used as the catalyst; the dehydration column (T-02) is 9 m in height, wherein the rectification section is 3 m while the stripping section (including the column kettle) 6 m; the column (T-03) is 26 m in height, wherein the rectification section is 10 m while the stripping section (including the column kettle) 16 m; the whole manufacturing process goes as follows:

Acetic acid and n-butanol, with mol ratio 1:1.1, are fed into the reaction section (6) after being heated by the preheaters (1 and 2), meanwhile the catalyst is mixed with the reactants and flushed into the reaction section as well; after 5 minutes' reaction therein, the mixed fluid flows through the filtering pipette, the pipe (6-21) and the pump (21); after being heated by the preheater (15), the fluid flows back to the reaction section (6) through the pipe (21-6) and the subsonic liquid jet agitator (33); the forced jet agitation occurs therein. The linear speed of the liquid in the jet agitator can be adjusted between 150 m/s and 360 m/s, and the general practice is at 260 m/s; thanks to its high vortical state, the fluid in the kettle can obtain ideal contact with the catalyst; keep the average reaction time of the fluid in the reaction section around 30 minutes, the time the reaction approximately reaches its balance; in the reaction section exists a filtering overflow pipe (7) that allows the liquid to overflow out while keeps the solid components therein; the overflowed fluid goes into the liquid distributor (8) through the valve (13) and the pipe (6-9); after being evenly distributed therein, the fluid flows into the stripping section (9) and the components in the fluid will be separated therein.

The gas emitting up from the stripping section goes into the rectification section (4) through the pipe (9-4) and the air distributor (5); after being separated therein, the gas is condensed into liquid in the condenser (12) at the column top; the liquid then goes into the oil-water separator (11) and will be separated therein; the oil-phase components include acetic acid (15.34%), butanol (40.46%), butyl acetate (44.22%) and a slight amount of water (<19 ppm); these oil-phase components flow back; the separated water then goes into the dehydration column (T-02) through the pipe (11-T-02) for further recovering the oil-phase components in it; the major component of the fluid going into the column (T-02) is water, containing a small amount of butyl acetate and n-butanol; after going through the condenser (22) at the column top and being condensed therein, the fluid goes into the oil-water separator (23) and will be separated therein; the oil-phase components include butanol (39%), butyl acetate (25), water (25%) and a small amount of acetic acid; these oil-phase components also flow back to the rectification section (4) of the column (T-01) through the pipe (23-4); the separated water, containing butanol (<42 ppm), butyl acetate (<1 ppm) and acetate acid (1.3%), is discharged from the bottom of the dehydration column (T-02);

The fluid that is channeled out from the stripping section (9) of the column (T-01) flows through the pipe (9-T-03) into the rectification column (T-03) for separation; the major components are n-butyl acetate, butanol, and some acetic acid; the gas gathering at the column top is condensed into liquid at the condenser (25) and collected by the liquid collector (26); part of the liquid flows back while the rest flows through the pipe (26-6) into the reaction section (6) of the catalytic reaction-rectification integrated column (T-01); the high concentration n-butyl acetate (99.95%) is discharged from the bottom of the column (T-03).

The system disclosed in this embodiment is able to increase the primary conversion rate of acetic acid up to 81%, 12% higher than sulfuric acid catalysis—a currently existing method; the reaction and separation procedures of this system is integrated as an organic whole so that the continuous operation is realized. The production capacity is therefore almost doubled, which in turn cuts down 24% on cost of butyl acetate production.

Embodiment 2

Production of Dihydromyrecenol through Hydration (3-Column System)

To produce dihydromyrcenol, a raw material for high-quality fragrance, through hydration of dihydromyrcene with catalysis of the acidic catalyst. The catalytic reaction-rectification integrated column (T-01) is 1.2 m in diameter and 28 m in height, wherein the reaction section (6) is 2.5 m in height while the rectification section (4) 14.5 m and the stripping section (9) (including the column kettle) 11 m; heat-resistant, high-acidic ion exchange resin is used as the catalyst; the column (T-02) is 25 m in height, wherein the rectification section is 10 m while the stripping section (including the column kettle) 15 m; the column (T-03) is 36 m in height, wherein the rectification section is 16 m while the stripping section (including the column kettle) 20 m; the whole manufacturing process goes as follows:

Dihydromyrcene solution (purity 88%) and water, with mol ratio 1:1.2?, are fed into the reaction section (6) after being heated by the preheaters (1 and 2); meanwhile the catalyst is mixed with the reactants and flushed into the reaction section as well; during reaction process, the reactant fluid is pumped out through the filtering pipette by the pump (21); after being heated by the preheater (15), the fluid flows back to the reaction section (6) through the subsonic liquid jet agitator (34); the forced jet agitation occurs therein. The linear speed of the liquid in the jet agitator (34) can be adjusted between 150 m/s and 360 m/s, and the general practice is around 330 m/s so that oil and water can be completely mixed; thanks to its high vortical state, the fluid in the reaction section can obtain ideal contact with the catalyst; keep the average reaction time of the fluid in the reaction section around 25 minutes, the time the reaction approximately reaches its balance; in the reaction section exists a filtering overflow pipe (7) that allows the liquid to overflow out while keeps the solid components therein; the overflowed fluid goes into the liquid distributor (8) through the valve (13) and the pipe (6-9); after being evenly distributed therein, the fluid flows into the stripping section (9) and the components in the fluid will be separated therein.

The gas emitting up from the stripping section goes through the pipe (9-4) into the rectification section (4); after being separated therein, the gas is condensed into liquid in the condenser (12) at the column top; the liquid then goes into the condensed liquid collector (11); the major components in the liquid are dihydromyrcenol, water and some light organics; part of the liquid flows back while the rest goes into the dehydration column (T-02) through the pipe (11-T-02) for further separation; the components obtained at the column top are water and some light organics (oil-phase); the gas collected therein is condensed in liquid at the condenser (22) and then flows into the oil-water separator (23) for phase-splitting; thereafter the water-phase components flow back while the oil-phase components are pumped out for storage. If the water-phase components are too much, they can also be channeled back to the reaction section (kettle).

The fluid, the major components of which are dihydromyrcenol and some heavy organics, is channeled out from the stripping section (9) of the column (T-01) and flows through the pipe (9-T-03) into the rectification column (T-03) for separation; the major component of the gas gathering at the column top is dihydromyrcenol, its purity reaches 99.5%; after being condensed in liquid at the condenser (25), it is collected by the condensed liquid collector (26); part of the condensed liquid flows back while the rest is channeled into the product storage tank for storage; the major components gathering at the bottom of the rectification column (T-03) are heavy organics; they are pumped out by a pump secured at the bottom of the rectification column (T-03) and stored in the storage tank designed for storage of heavy organics.

The system disclosed in this embodiment is able to increase the primary conversion rate of dihydromyrcene up to 88%, 18% higher than fixed-bed catalytic hydration—a currently existing method; in addition, the reaction time is shortened to one third of that of fixed-bed catalytic hydration; the reaction and separation procedures of this system is integrated as an organic whole so that the continuous operation is realized. The production capacity is therefore almost doubled, which in turn cuts down 56% on cost of dihydromyrcenol production.

Embodiment 3

Production of MTBE through etherification of Methanol and Isobutylene (2-Column System)

To produce methyl tertiary butyl ether (MTBE), a very important chemical product, through etherification of methanol and isobutylene with catalysis of AMBERLYST-15 (a catalyst provided by Tianjin Wisdom International Trade Co., Ltd). The catalytic reaction-rectification integrated column is 0.3 m in diameter and 18 m in height, wherein the reaction section (6) is 1.2 m in height while the rectification section (4) 8 m and the stripping section (9) (including the column kettle) 8.8 m; the dehydration column (T-02) is 35 m in height, wherein the rectification section is 15 m while the stripping section (including the column kettle) 20 m; the whole manufacturing process goes as follows:

Methanol solution (industrial grade) is fed into the reaction section (6) of the reaction-rectification integrated column (T-01) after being heated by the preheaters (1); meanwhile the catalyst is mixed in and flushed into the reaction section as well; the other raw material butylene, after being gasified by the preheater (2), is fed into the reaction section (6) through the pipe connecting to the reaction section (6) at the bottom; the reactant fluid in the reaction section (6) is pumped out through the filtering pipette by the pump (21); after going through the pipe (6-21) and being heated by the preheater (15), the fluid flows back to the reaction section (6) through the subsonic liquid jet agitator (33); the forced jet agitation occurs therein. The linear speed of the liquid in the jet agitator (33) can be adjusted between 150 m/s and 360 m/s, and the general practice is around 350 m/s so that gas and liquid can be completely mixed; When the jet agitator starts working, negative pressure occurs around the suction inlet, which connects to the pipe (12) at the top cover of the reaction section (6); the pipe will suction out the gas-phase mixture—mainly isobutylene—that have not reacted yet, and send it back into the jet agitator (33) so that it can mix with liquid jet there and undergoes reaction at the middle and lower part of the reaction section (6) again; this circulation is what differentiates this embodiment from the other two; thanks to its high vortical state, the fluid in the reaction section can obtain ideal contact with the catalyst; a complete reaction can be achieved as far as the gas-liquid mixture is provided an appropriate average reaction time; in the reaction section exists a filtering overflow pipe (7) that allows the liquid to overflow out while keeps the solid components therein; the overflowed fluid goes into the liquid distributor (8) through the valve (13) and the pipe (6-9); after being evenly distributed therein, the fluid flows into the stripping section (9) and the components in the fluid will be separated therein.

The gas emitting up from the stripping section goes through the pipe (9-4) into the rectification section (4); after being separated therein, part of the gas is condensed into liquid while the rest goes through a specially designed washer (27) so that methanol can be washed and absorbed; the insoluble gas-phase components (other C4 components) are channeled into the storage tank or specially designed pipe system; the methanol solution is sent into the dehydration column (T-02) for separation; the methanol will be recovered at the column top while water gathers at the column bottom; the water is discharged out of the column after being comprehensively utilized.

The major components of the fluid channeled into the stripping section (9) of the reaction-rectification integrated column (T-01) are MTBE and some others that share the same boiling point with MTBE; after being completely separated in the stripping section (9), MTBE is pumped out from the bottom of the column.

The system disclosed in this embodiment is able to increase the conversion rate of isobutylene up to 99.9%, much higher than fixed-bed catalytic esterification, or agitated gas bubbling gas-liquid esterification; in addition, it increases selectivity of reaction and shortens the reaction time; compared with the fixed-bad catalytic esterification, the reaction time is shorten about 40%; the reaction and separation procedures of this system is integrated as an organic whole so that the continuous operation is realized and byproduct heat can be comprehensively utilized; both the production capacity and utilization rate of heat energy obtain remarkable increase.

The invention claimed is:

1. A process integrating catalytic reaction and rectification, comprising the following steps:

leading two reactants that are separately stored in storage tanks to preheaters, and pre-mixed with a solid catalyst, introducing the two reactants through a feeding pipe into a jet agitation reaction section, which is a reactor, in a middle of a catalytic reaction-rectification integrated column;

flowing the two reactants in the jet-agitation reaction section through a filtering bottom socket and a first pipe to a centrifugal pump; wherein, pressurizing by the centrifugal pump, the two reactants to be at least one of heated and cooled by going through a heat exchanger and then led into a subsonic or transonic jet agitator of the jet-agitation reaction section; further wherein the two reactants are jetted into the jet-agitation reaction section at a high speed to mix a solid and a liquid in the jet-agitation reaction section;

providing a filtering overflow pipe in the jet-agitation reaction section; wherein, when the fluid therein reaches a certain level, the fluid overflows down through a pipe into a liquid distributor at a lower part of the catalytic reaction-rectification integrated column; further wherein, after being distributed therein, the fluid is introduced into a stripping section of the catalytic reaction-rectification integrated column;

fractionally distilling and separating the fluid in the stripping section of the catalytic reaction-rectification integrated column, and thereafter is channeled from a bottom of the catalytic reaction-rectification integrated column; wherein a part of the fluid is fed to a stripping column for further separation while the rest is heated into steam by a first reboiler, and is subsequently channeled back to the stripping section of the catalytic reaction-rectification integrated column;

leading the gas evaporating from the stripping section of the catalytic reaction-rectification integrated column through a second pipe and an air distributor back to a rectification section of the catalytic reaction-rectification integrated column for further separation, while a precipitating fluid in the rectification section directly flows into the jet-agitation reaction section of the catalytic reaction-rectification integrated column for further processing; wherein the gas separated by the rectification section is condensed into liquid by a first condenser at a column top; the condensed liquid is then introduced goes into an oil-water separator for oil-water phase-splitting; the oil-phase components flow back to a top of the rectification section of the catalytic reaction-rectification integrated column while the water-phase components are channeled into a dehydration column, wherein the water-phase components are dehydrated so that the oil-phase components in the water-phase components are further extracted, leading the fluid, after being separated through dehydration in the dehydration column, to the column top, wherein the fluid is condensed by a second condenser and channeled to the oil-water separator for phase-splitting; wherein the water-phase components then flow into a top of the dehydration column while the oil-phase components flow back to the rectification section of the catalytic reaction-rectification integrated column through a third pipe and the water-phase components that flow into the dehydration column, after being upgradingly purified, is discharged through a fourth pipe at the bottom of the dehydration column; and further separating the fluid, after the fractionally distilling and separating step by the rectification column; wherein the gas obtained is condensed into liquid by a third condenser at the top of the column; the liquid then comes into a collector, part of which flows back while the rest returns to the jet-agitation reaction section of the column again or to a storage tank; further wherein the fluid at the bottom of the rectification column is the high boiling point distillate, part of which is channeled back to the storage tank through a fifth pipe on a base of the column, while the rest is heated into steam by a second reboiler and led to the bottom of the rectification column.

2. The process of integrating catalytic reaction and rectification as defined in claim 1, wherein the solid catalyst is changed after a certain period of operation, the steps include:

turning off a first valve on the first pipe connecting the reaction section and the centrifugal pump and then turning on both a second valve on a pipe connecting the bottom of the reaction section and a catalyst solid-liquid separation tank and a third valve on a pipe connecting the catalyst solid-liquid separation tank and the centrifugal pump; the catalyst solid-liquid separation tank secures a filtering mesh, which retains the solid catalyst grains of the solid catalyst in the fluid while letting the fluid go; wherein the fluid then is pumped back to the jet-agitation reaction section through the first pipe by the centrifugal pump;

turning off both the second valve and the third valve after the catalyst in the jet-agitation reaction section is completely channeled into the catalyst solid-liquid separation tank;

providing a catalyst feed equipment on a pipe connecting the storage tanks and the jet-agitation reaction section of the catalytic reaction-rectification integrated column, and opening a cover of the catalyst feeding equipment and adding new catalyst grains then closing the cover;

turning on a valve of the catalyst feeding equipment and turning on a valve on the pipe connecting the storage tanks and the jet-agitation reaction section of the catalytic reaction-rectification integrated column; along with a current of liquid reactants from the tanks to the jet-agitation reaction section, the catalyst grains in the catalyst feeding equipment is flushed into the jet-agitation reaction section of the catalytic reaction-rectification integrated column; and turning off the valve of the catalyst feeding equipment and the valve on the pipe connecting the storage tanks, and removing the catalyst from the catalyst solid-liquid separation tank; wherein the whole procedure of changing catalyst is accomplished, and then resumes its normal process.

3. The process of integrating catalytic reaction and rectification as defined in claim 1, wherein esters are produced through combination of acids and alcohols, alcohols through hydration of olefins, or ethers through combination of olefins and alcohols.

4. A catalytic reaction-rectification integrated column specially designed for the process integrating catalytic reaction and rectification as defined in claim 1, comprising three sections: the upper rectification section, the middle jet agitation reaction section and the lower stripping section; the rectification section is a fractional distilling column in the form of either a plate column or a packing column, the bottom of which exists an air distributor while the top of which exist a condenser and oil-water separator; the jet agitation reaction section has a base and a top cover that can be either porous or airtight; at the upper of the jet agitation reaction section exist a feeding inlet and a feeding pipe; in the middle of the jet agitation reaction section exist a subsonic or transonic jet agitator and a filtering pipette that connects to the centrifugal pump; an outlet of the centrifugal pump connects to the jet agitator; when starting the centrifugal pump, the fluid in the jet agitation reaction section circulates therein continuously, and strong jet reaction occurs as well; in the jet agitation reaction section also exists a filtering overflow pipe that connects to the liquid distributor at the top of the stripping section; when the fluid in the reaction section reaches a certain level, it automatically overflows down to the liquid distributor at the top of the stripping section, then to the stripping section; the stripping section is also a fractional distilling column in the form of either a plate column or a packing column; on the base of the column connects a pipe that channels out the primarily processed fluid, part of which is reheated by the reheater and flows back to the lower part of the stripping section; the steam at the upper part of the stripping section via the outer pipe, is led to the air distributor at the bottom of the rectification section; the steam is rectified therein; the high boiling point distillate at the bottom of the rectification section then flows back to the jet-agitation reaction section.

5. The catalytic reaction-rectification integrated column as defined in claim 4, wherein the rectification section is a plate column.

6. The catalytic reaction-rectification integrated column as defined in claim 4, wherein the stripping section is a packing column.

7. The catalytic reaction-rectification integrated column as defined in claim 4, wherein on the feeding pipe that is on the top of the jet agitation reaction section secure a catalyst feeding equipment and a valve; at the bottom of the column exists a pipe connecting to the catalyst solid-liquid separation tank, which has a pipe connecting to the centrifugal pump; there is a filtering mesh in the catalyst solid-liquid separation tank for changing the catalyst.

\* \* \* \* \*

UNITED STATES PATENT AND TRADEMARK OFFICE
CERTIFICATE OF CORRECTION

| | | |
|---|---|---|
| PATENT NO. | : 8,721,842 B2 | Page 1 of 1 |
| APPLICATION NO. | : 12/745709 | |
| DATED | : May 13, 2014 | |
| INVENTOR(S) | : Zhang et al. | |

It is certified that error appears in the above-identified patent and that said Letters Patent is hereby corrected as shown below:

In the Claims:

COLUMN 11

Line 1, delete "goes"

Line 52, after "providing" delete "a"

COLUMN 12

Line 22, after "top of which" delete "exist" and insert -- exists --

Line 25, delete "exist" and insert -- exists --

Line 27, delete "exist" and insert -- exists --

Signed and Sealed this
Second Day of September, 2014

Michelle K. Lee
*Deputy Director of the United States Patent and Trademark Office*